United States Patent [19]
Kondo et al.

[11] Patent Number: 5,853,981
[45] Date of Patent: Dec. 29, 1998

[54] OLIGONUCLEOTIDES, METHODS AND KITS FOR AMPLIFYING AND DETECTING A NUCLEIC ACID OF CYTOMEGALOVIRUS (CMV) USING NUCLEIC ACID SEQUENCE $\beta 2.7$

[75] Inventors: Motohiro Kondo; Toshiya Aono; Masaya Segawa, all of Ohtu; Koichi Yamanishi; Kazuhiro Kondo, both of Osaka; Keiko Taya, Suita, all of Japan

[73] Assignee: Toyo Boseki Kabushiki Kaisha, Osaka, Japan

[21] Appl. No.: 839,306

[22] Filed: Apr. 18, 1997

[30] Foreign Application Priority Data

Apr. 26, 1996 [JP] Japan ................................. 8-107789

[51] Int. Cl.$^6$ ........................................................ C12Q 1/70
[52] U.S. Cl. ................................ 435/5; 435/6; 435/91.2; 436/501; 536/22.1; 536/23.1; 536/24.1; 536/24.3; 536/24.31; 536/24.32; 536/24.33; 935/77; 935/78
[58] Field of Search ..................... 435/5, 6, 810, 435/91.2; 436/501; 536/22.1, 23.1, 24.1, 24.3–24.33; 935/77, 78

[56] References Cited

U.S. PATENT DOCUMENTS 5,409,818  4/1995  Davey et al. ......................... 435/91.21

OTHER PUBLICATIONS

Kondo et al, "Human cytomegalovirus latent infection of granulocyte–macrophage progenitors", Proc. Natl. Acad. Sci. USA, vol. 91, pp. 11879–11883, Dec. 1994.

Sooknanan et al, "NASBA, A detection and amplification system uniquely suited for RNA", Biotechnology, vol. 13, pp. 563–564, Jun. 1995.

Vandamme et al, "Detection of HIV–1 RNA in plasma and serum samples using the NASBA amplification system compared to RNA–PCR", J. of Virol. Meth., vol. 52, pp. 121–132, 1995.

*Primary Examiner*—Ardin H. Marschel
*Attorney, Agent, or Firm*—Foley & Lardner

[57] ABSTRACT

The present invention relates to two primers for amplifying a cytomegalovirus (CMV) nucleic acid suitable for a nucleic acid sequence-based amplification (NASBA) using a DNA-dependent RNA polymerase, a first primer containing a promoter sequence and a nucleic acid sequence consisting of at least fifteen continuous bases selected from the nucleic acid sequence of SEQ ID NO:1; a second primer containing a nucleic acid sequence consisting of at least fifteen continuous bases selected from the nucleic acid sequence of SEQ ID NO:2, NO:3 or NO:4; a detecting probe and/or a capturing probe containing a nucleic acid sequence consisting of at least continuous fifteen bases selected from the nucleic acid sequence(s) of SEQ ID NO:5, NO:6 and/or NO:7 wherein said sequence is modified if necessary; a reagent kit for detecting a CMV containing the above-mentioned primers and probes; and a nucleic acid sequence-based amplification (NASBA) using said primers. The advantages of the present invention are that CMV can be detected in an easy, rapid and specific manner with a high sensitivity.

32 Claims, 1 Drawing Sheet

OLIGONUCLEOTIDES, METHODS AND KITS FOR AMPLIFYING AND DETECTING A NUCLEIC ACID OF CYTOMEGALOVIRUS (CMV) USING NUCLEIC ACID SEQUENCE β2.7

TECHNICAL FIELD OF THE INVENTION

The present invention relates to a reagent kit for amplification and detection of nucleic acid of cytomegalovirus (CMV) utilizing a nucleic acid sequence (β2.7) and also to a method for amplifying and detecting a nucleic acid of cytomegalovirus (CMV) simply and rapidly using such a reagent.

PRIOR ART

Cytomegalovirus (hereinafter, abbreviated as CMV) is a virus belonging to a family Herpesviridae and belongs to β herpesvirus in view of its cell tropism, proliferation cycle and latent mode. The characteristic feature is that, after its primary infection, CMV causes latent infection in a host until its end of life, and this virus is reactivated by the physiological changes of the host. In the patients suffering from cancer and AIDS and transplant recipients who are anticipated to increase in future, the immunocompromised state is a cause of reactivation of CMV resulting in a problem with an onset of interstitial pneumonia, hepatitis, retinitis, encephalitis or nephritis.

As such, infection and reactivation of CMV are large problems as the present-day diseases and it is important for an early therapy to establish a diagnostic method in an early stage. Until now, a virus culture method has been known as a diagnostic method for CMV infection but it requires a period of as long as several weeks and therefore is lacking in quickness. In a serum diagnostic method in which an anti-CMV antibody is detected from the serum of the patient, there are problems that a reaction which is not specific to the antibody occurs and that a high sensitivity is not resulted and, in addition, there is a disadvantage that it is difficult to follow the virus because of the changes in antibody values.

As a result of the progress of molecular biology in recent years, it has been possible to detect CMV DNA by means of an in situ DNA hybridization or by a polymerase chain reaction (PCR). The former is a method in which a labeled DNA probe complementary with CMV sequence is used to hybridize with tissue samples or cultured cells whereby a viral DNA is identified. The latter, i.e. a PCR is a method in which a CMV-specific primer is used whereby viral DNA in a small amount is amplified by means of a polymerase reaction. The PCR method is especially characteristic in its very high sensitivity and excellent quickness. Unfortunately, CMV infects latently to various organs in a form of DNA and, therefore, it is not possible to distinguish between active infection and latent infection only by the detection of CMV DNA by a PCR.

Under such circumstances, a method for detecting the CMV DNA from cell-free serum by a PCR was proposed but that is not useful for diagnosis in an early stage. In addition, a reverse transcription PCR method in which mRNA which is present during viral replication is detected was considered but, in this method, it is necessary to remove DNA completely existing in the sample prior to the PCR and convert the mRNA to DNA by reverse reaction. Thus, this method is troublesome. Moreover, when DNA remains even in a small amount, there is a risk that the result is judged to be positive even if mRNA is not present.

On the other hand, an NASBA (nucleic acid sequence-based amplification) has been receiving public attention in recent years as an amplifying method using an RNA polymerase which specifically amplifies the RNA (refer to the Japanese Laid-Open Patent Publications Hei-2/5864 and Hei-4/501057). In an NASBA method, RNA(-) is amplified only from RNA(+) which is basically a template and, therefore, when mRNA which is not expressed in latent infection but is expressed only in active infection is selected, then it is possible to specifically detect the active CMV. The mRNA which is transcribed from the DNA exists in a large amount as compared with the genome DNA and, accordingly, construction of the system with a higher sensitivity can be expected. Moreover, a system for detecting the mRNA in the active infection is useful in the monitoring of the therapeutic effect by ganciclovir, etc.

Problems To Be Solved By the Invention

An object of the present invention is to provide an oligonucleotide which is capable of amplifying and detecting a CMV nucleic acid by means of an NASBA method in an easy, rapid and specific manner with a high sensitivity. To be more specific, the present invention is to provide amplifying primers suitable for the NASBA method and also a capturing probe or a detecting probe for identifying the amplified product obtained by said primers whereby the problems in the conventional clinical test methods for CMV have now been solved.

Means To Solve the Problems

The present inventors have conducted an intensive study on genes of CMV and, as a result, they have paid their attention to the fact that β2.7 transcript of CMV does not express in latent infection but expresses in a large amount only in active infection and have established a detection method using amplifying primers and capturing probe and/ or detecting probe having a sequence which is capable of amplifying in an easy, rapid and specific manner with a high sensitivity from RNA which is a transcript of β2.7 gene of CMV whereupon the present invention has been achieved.

Thus, the present invention relates to an oligonucleotide for amplifying a nucleic acid of cytomegalovirus (CMV) utilizing a nucleic acid sequence (β2.7), said oligonucleotide containing a nucleic acid sequence consisting of at least fifteen continuous bases selected from the nucleic acid sequence of SEQ ID NO:1.

Further, the present invention relates to an oligonucleotide for amplifying a nucleic acid of cytomegalovirus (CMV) utilizing a nucleic acid sequence (β2.7), said oligonucleotide containing a nucleic acid sequence consisting of at least fifteen continuous bases selected from the nucleic acid sequence of SEQ ID NO:2, NO;3, or NO:4.

Still further, the present invention relates to an oligonucleotide for amplifying a nucleic acid of cytomegalovirus (CMV) utilizing a nucleic acid sequence (β2.7), said oligonucleotide linking a promoter sequence of DNA-dependent RNA polymerase at the 5'-terminal of oligonucleotide as mentioned hereinabove.

The present invention also relates to oligonucleotides for amplifying a nucleic acid of cytomegalovirus (CMV) utilizing a nucleic acid sequence (β2.7), said oligonucleotides comprising an oligonucleotide containing a nucleic acid sequence consisting of at least fifteen continuous bases selected from the nucleic acid sequence of SEQ ID NO:1 and an oligonucleotide containing a nucleic acid sequence consisting of at least fifteen continuous bases selected from the nucleic acid sequence of SEQ ID NO:2, NO;3, or NO:4, wherein at least one of said oligonucleotide has a promoter sequence of a DNA-dependent RNA polymerase at the 5'-terminal.

The present invention also relates to a reagent kit for amplifying a nucleic acid of cytomegalovirus (CMV), said reagent kit comprising;

(a) a first primer for amplifying a nucleic acid of cytomegalovirus (CMV) which contains a nucleic acid sequence consisting of at least fifteen continuous bases selected from the nucleic acid sequence of SEQ ID NO:1 and has a promoter sequence of a DNA-dependent RNA polymerase at the 5'-terminal, (b) a second primer for amplifying a nucleic acid of cytomegalovirus (CMV) which contains a nucleic acid sequence consisting of at least fifteen continuous bases selected from the nucleic acid sequence of SEQ ID NO:2, NO:3 or NO:4, (c) a substance having an RNA-dependent DNA polymerase activity, (d) a substance having a ribonuclease H activity, (e) a substance having an DNA-dependent DNA polymerase activity, (f) a substance having an DNA-dependent RNA polymerase activity, (g) ribonucleoside triphosphates and (h) deoxyribonucleoside triphosphates.

Further, the present invention relates to a reagent kit for amplifying a nucleic acid of cytomegalovirus (CMV), said reagent kit comprising;

(a) a first primer for amplifying a nucleic acid of cytomegalovirus (CMV) which contains a nucleic acid sequence consisting of at least fifteen continuous bases selected from the nucleic acid sequence of SEQ ID NO: 2, NO:3 or NO:4 and has a promoter sequence of a DNA-dependent RNA polymerase at the 5'-terminal, (b) a second primer for amplifying a nucleic acid of cytomegalovirus (CMV) which contains a nucleic acid sequence consisting of at least fifteen continuous bases selected from the nucleic acid sequence of SEQ ID NO:1, (c) a substance having an RNA-dependent DNA polymerase activity, (d) a substance having a ribonuclease H activity, (e) a substance having an DNA-dependent DNA polymerase activity, (f) a substance having an DNA-dependent RNA polymerase activity (g) ribonucleoside triphosphates and (h) deoxyribonucleoside triphosphates.

Still further, the present invention relates to a reagent kit for amplifying a nucleic acid of cytomegalovirus (CMV), said reagent kit comprising;

(a) a first primer for amplifying a nucleic acid of cytomegalovirus (CMV) which contains a nucleic acid sequence consisting of at least fifteen continuous bases selected from the nucleic acid sequence of SEQ ID NO:1and has a promoter sequence of a DNA-dependent RNA polymerase at the 5'-terminal, (b) a second primer for amplifying a nucleic acid of cytomegalovirus (CMV) which contains a nucleic acid sequence consisting of at least fifteen continuous bases selected from the nucleic acid sequence of SEQ ID NO:2, NO:3 or NO:4 and has a promoter sequence of a DNA-dependent RNA polymerase at the 5'-terminal, (c) a substance having an RNA-dependent DNA polymerase activity, (d) a substance having a ribonuclease H activity, (e) a substance having an DNA-dependent DNA polymerase activity, (f) a substance having an DNA-dependent RNA polymerase activity, (g) ribonucleoside triphosphates and (h) deoxyribonucleoside triphosphates.

The present invention also relates to a method for amplifying a nucleic acid of cytomegalovirus (CMV) utilizing a nucleic acid sequence ($\beta$2.7), which method comprises the following steps (l)to (10);

(1) extracting a target nucleic acid consisting of RNA (+) from a sample if necessary;

(2) hybridizing a first primer for amplifying a nucleic acid of cytomegalovirus (CMV) which contains a nucleic acid sequence consisting of at least fifteen continuous bases selected from the nucleic acid sequence of SEQ ID NO:1 and has a promoter sequence of a DNA-dependent RNA polymerase at the 5'-terminal with an RNA (+) as a template to elongate the primer by the RNA-dependent DNA polymerase whereupon an elongated RNA/DNA hybrid is obtained, (3) digesting the RNA in the elongated RNA/DNA hybrid by a ribonuclease H which specially digests only the RNA of the elongated RNA/DNA hybrid whereupon a single-stranded DNA is obtained, (4) hybridizing a second primer for amplifying a nucleic acid of cytomegalovirus (CMV) which contains a nucleic acid sequence consisting of at least fifteen continuous bases selected from the nucleic acid sequence of SEQ ID NO:2, NO:3 or NO:4 with said single-stranded DNA as a template to perform a DNA elongation reaction by a DNA-dependent DNA polymerase whereupon a double-stranded DNA intermediate having a functionable promoter sequence at the upstream of the 5'-terminal is produced, (5) transcribing a single-stranded RNA (-) increasingly from said-double stranded DNA intermediate by the DNA-dependent RNA polymerase which is capable of recognizing the above mentioned promoter sequence, (6) hybridizing the second primer for amplifying a nucleic acid of cytomegalovirus (CMV) which contains a nucleic acid sequence consisting of at least fifteen continuous bases selected from the nucleic acid sequence of SEQ ID NO:2, NO:3 or NO:4 with the single stranded RNA (-) obtained in the above step as a template to perform a DNA elongation reaction by a RNA-dependent DNA polymerase whereupon an elongated RNA/DNA hybrid is obtained, (7) digesting the RNA in the elongated RNA/DNA hybrid by a ribonuclease H which specially digests only the RNA of the elongated RNA/DNA hybrid whereupon a single-stranded DNA is obtained, (8) hybridizing the first primer for amplifying a nucleic acid of cytomegalovirus (CMV) which contains a nucleic acid sequence consisting of at least fifteen continuous bases selected from the nucleic acid sequence of SEQ ID NO:1 and has a promoter sequence of a DNA-dependent RNA polymerase at the 5'-terminal with said single-stranded DNA as a template to perform a DNA elongation reaction by a DNA-dependent DNA polymerase whereupon a double-stranded DNA intermediate having a functionable promoter sequence at the upstream of the 5'-terminal is produced, (9) transcribing the single-stranded RNA (-) increasingly from said double-stranded DNA intermediate by the DNA-dependent RNA polymerase which is capable of recognizing the above mentioned promoter sequence, and (10) if necessary, repeating the above mentioned steps (6) to (9) using the resulting single stranded RNA (-) as a template.

The present invention relates to a method for amplifying a nucleic acid of cytomegalovirus (CMV) utilizing a nucleic acid sequence (β2.7), which method comprises the following steps (1)to (10);

(1) extracting a target nucleic acid consisting of RNA (+) from a sample if necessary;

(2) hybridizing a first primer for amplifying a nucleic acid of cytomegalovirus (CMV) which contains a nucleic acid sequence consisting of at least fifteen continuous bases selected from the nucleic acid sequence of SEQ ID NO:1and has a promoter sequence of a DNA-dependent RNA polymerase at the 5'-terminal with an RNA (+) as a template to elongate the primer by the RNA-dependent DNA polymerase whereupon an elongated RNA/DNA hybrid is obtained, (3) digesting the RNA in the elongated RNA/DNA hybrid by a ribonuclease H which specially digests only the RNA of the elongated RNA/DNA hybrid whereupon a single-stranded DNA is obtained, (4) hybridizing a second primer for amplifying a nucleic acid of cytomegalovirus (CMV) which contains a nucleic acid sequence consisting of at least fifteen continuous bases selected from the nucleic acid sequence of SEQ ID NO:2, NO:3 or NO:4 and has a promoter sequence of a DNA-dependent RNA polymerase at the 5'-terminal with said single-stranded DNA as a template to perform a DNA elongation reaction by a DNA-dependent DNA polymerase whereupon a double- stranded DNA intermediate having a functionable promoter sequence at the upstream of the 5'-terminal is produced, (5) transcribing a single-stranded RNA (-) increasingly from said-double stranded DNA intermediate by the DNA-dependent RNA polymerase which is capable of recognizing the above mentioned promoter sequence, (6) hybridizing the second primer for amplifying a nucleic acid of cytomegalovirus (CMV) which contains a nucleic acid sequence consisting of at least fifteen continuous bases selected from the nucleic acid sequence of SEQ ID NO:1and has a promoter sequence of a DNA-dependent RNA polymerase at the 5'-terminal with the single stranded RNA (-) obtained in the above step as a template to perform a DNA elongation reaction by a RNA-dependent DNA polymerase whereupon an elongated RNA/DNA hybrid is obtained, (7) digesting the RNA in the elongated RNA/DNA hybrid by a ribonuclease H which specially digests only the RNA of the elongated RNA/DNA hybrid whereupon a single-stranded DNA is obtained, (8) hybridizing the first primer for amplifying a nucleic acid of cytomegalovirus (CMV) which contains a nucleic acid sequence consisting of at least fifteen continuous bases selected from the nucleic acid sequence of SEQ ID NO: 2, NO:3 or NO:4 and has a promoter sequence of a DNA-dependent RNA polymerase at the 5'-terminal with said single-stranded DNA as a template to perform a DNA elongation reaction by a DNA-dependent DNA polymerase whereupon a double- stranded DNA intermediate having a functionable promoter sequence at the upstream of both terminals is produced, (9) transcribing the single-stranded RNA(-) and RNA(+) increasingly from said double-stranded DNA intermediate by the DNA-dependent RNA polymerase which is capable of recognizing the above mentioned promoter sequence, and (10) if necessary, repeating the above mentioned steps (6) to (9) using the resulting single stranded RNA(-) and RNA(+) as a template.

The present invention relates to a probe for detecting and/or capturing a nucleic acid of the cytomegalovirus (CMV), said probe containing a nucleic acid sequence consisting of at least fifteen continuous bases selected from the nucleic acid sequence of SEQ ID NO:5, NO:6 and/or NO:7 or complementary nucleic acid thereof or said nucleic acid being modified if necessary.

The present invention also relates to a reagent kit for detecting a nucleic acid of the cytomegalovirus (CMV), said reagent kit comprising a reagent kit for amplifying a nucleic acid of the above-mentioned cytomegalovirus (CMV), and further a probe for detecting and/or capturing a nucleic acid of the cytomegalovirus (CMV) which contains a nucleic acid sequence consisting of at least fifteen continuous bases selected from the nucleic acid sequence of SEQ ID NO:5, NO:6 and/or NO:7 or complementary nucleic acid thereof or said nucleic acid being modified if necessary.

The present invention also relates to a method for detecting a nucleic acid of the cytomegalovirus (CMV) utilizing a nucleic acid sequence (β2.7), which comprises detecting nucleic acids amplified by the above-mentioned method with a probe for detecting and/or capturing a nucleic acid of the cytomegalovirus (CMV) containing a nucleic acid sequence consisting of at least fifteen continuous bases selected from the nucleic acid sequence of SEQ ID NO:5, NO:6 and/or NO:7 or complementary nucleic acid thereof or said nucleic acid being modified by a label.

Further, the present invention relates to a method for detecting a nucleic acid of the cytomegalovirus (CMV) utilizing a nucleic acid sequence (β2.7), which method comprises hybridizing nucleic acids amplified by the above-mentioned method with a capturing probe absorbed or bound with solid support wherein a nucleic acid sequence consisting of at least fifteen continuous bases selected from the nucleic acid sequence of SEQ ID NO:5, NO:6 and/or NO:7 and optionally modified and a detecting probe wherein a nucleic acid sequence consisting of at least fifteen continuous bases selected from the nucleic acid sequence of SEQ ID NO:5, NO:6 and/or NO:7 which is modified by a label, then separating the unreacted detecting probe and measuring a label of a conjugate of capturing probe, amplified nucleic acids and detecting probe.

Then the terms used in the present invention will be explained as hereunder. "Promoter sequence" is a nucleic acid sequence to which the DNA-dependent RNA polymerase specifically binds. The DNA-dependent RNA polymerase synthesizes the RNA homologous to the DNA sequence which is downstream from the promoter sequence. "A method of amplifying the nucleic acid using a DNA-dependent RNA polymerase" is that the promoter sequence of the DNA-dependent RNA polymerase sequence is contained in the primer used for the synthesis of a double-stranded DNA from a target nucleic acid (DNA) whereupon, succeeding to the synthesis of the double-stranded DNA, the RNA corresponding to the target nucleic acid (DNA) is synthesized by a DNA-dependent RNA polymerase using the synthesized double- stranded DNA as a template.

This is also a method of performing an RNA transcription reaction for synthesizing the RNA wherein a DNA/RNA hybrid is synthesized from the synthesized RNA using an RNA-dependent DNA polymerase, then the RNA of this hybrid is digested to give a single-stranded DNA and finally a double-stranded DNA containing a promoter sequence of the DNA-dependent RNA polymerase is synthesized from the single-stranded DNA prepared as such and the primer containing the above-mentioned promoter sequence.

"NASBA method" is that RNA/DNA hybrid is synthesized by RNA- dependent DNA polymerase from a target nucleic acid (RNA) with a primer (P1) having promoter sequence of the DNA-dependent RNA polymerase and then RNA strand of this hybrid is digested by ribonuclease H to remain DNA strand. A double-stranded DNA is synthesized from the remaining DNA of the hybrid with an another primer (P2) different from the above-mentioned primer and DNA- dependent DNA polymerase. A lot of RNAs complementary to the target nucleic acid are transcribed from the double-stranded DNA by DNA- dependent RNA polymerase. The next is that RNA/DNA hybrid is synthesized from the said complementary RNA with a primer (P2) by RNA-dependent DNA polymerase and then RNA strand of this hybrid is digested by ribonuclease H, wherein a single-stranded DNA is obtained. From this single-stranded DNA and said primer (P1) having a promoter sequence of the DNA-dependent RNA polymerase a double- stranded DNA having the promoter sequence is synthesized and RNA transcription that produces RNA complementary to target nucleic acid is performed again.

The NASBA method includes a method wherein a target nucleic acid (DNA) is transcribed to RNA and then a usual NASBA method is performed.

The NASBA method is characterized in using ribonuclease H in a method of separating the DNA on a duplicated RNA base. According to this method, it is possible to transcribe several tens to several thousands molecules of RNA from one molecule of a double-stranded nucleic acid (DNA) using a DNA-dependent RNA polymerase and an efficiency of amplifying the nucleic acid per cycle is high as compared with the PCR method. In addition, as a result of the use of ribonuclease H, the temperature cycle which is necessary in the PCR method is no longer necessary whereby it is possible to amplify the nucleic acid (RNA) in an easier and simpler manner.

"Modification" means that another nucleotide is added to or substituted for at least one nucleotide in the oligonucleotide. The term "add(ed)" means that nucleotide, oligo dGTP, oligo DATP, oligo dTTP, oligo dCTP, etc. having fluorescence substance, linker arm, biotin, etc. are bound to a 5'-terminal or a 3'-terminal of the oligonucleotide sequence. The term "substitute(d)" means that nucleotide having fluorescence substance, linker arm, biotin, etc. is introduced as a substitute for at least one nucleotide in the oligonucleotide. Introduction of known labels such as radioactive substances, enzymes, fluorescence substances, etc. after synthesis of oligonucleotide is also included therein.

"Label" is a substance which is detectable as it is such as radioactive substances, enzymes, fluorescence substances, etc. It also covers a substance which is capable of binding with such a detectable substance.

EMBODIMENTS OF THE INVENTION

The target nucleic acid to be detected in accordance with the present invention may be either DNA or RNA. It is subjected to an amplifying reaction after changing it to a single-stranded chain by a modifying treatment such as heating or treating with acid or alkali in the case of a double-stranded chain or even in the case of a single-stranded chain if it is in a high-order structure.

When the target nucleic acid is present in a mixture of protein, lipid, saccharide, etc. or in a biological sample, the target nucleic acid is extracted by a conventional methods and then utilized to the amplification and detection of the present invention.

A specific example of the extracting method is that a solution containing proteinase, detergent, etc. is added to the sample, an incubation is carried out for about 30 minutes, the resulting solution is extracted with phenol, chloroform or the like and the extract is treated with ethanol to precipitate the nucleic acid. Another example is to use a method described by Boom et al. (cf. J. Clin. Microbiol. 28:495–503). Thus, for example, a cultured cell liquid of the cells infected by CMV (AD 169 strain) is treated in a buffer for solubilization containing Triton X-100 and guanidium thiocyanate (GuSCN) and silica particle is added thereto to adsorb the mRNA. Then the silica particle adsorbing the mRNA is washed twice to thrice with a buffer for washing containing GuSCN, then GuSCN is removed with acetone and the residue is dried. Elution is carried out using distilled water containing neither ribonuclease (RNase) nor deoxyribonuclease (DNase). The eluate may be subjected to a gradient dilution with the same distilled water.

The primer for amplification in accordance with the present invention includes a nucleic acid sequence consisting of at least fifteen continuous bases selected from the nucleic acid sequence mentioned in SEQ ID NO:1 of the Sequence Listing or a nucleic acid sequence consisting of at least fifteen continuous bases selected from the nucleic acid sequence mentioned in SEQ ID NO:2, NO:3 or NO:4 of the Sequence Listing.

The capturing probe or the detecting probe of the present invention includes a nucleic acid sequence consisting of at least fifteen continuous bases selected from the nucleic acid mentioned in SEQ ID NO: 5, NO: 6 or NO: 7 of the Sequence Listing wherein said nucleic acid may be modified if necessary.

Figure 1:
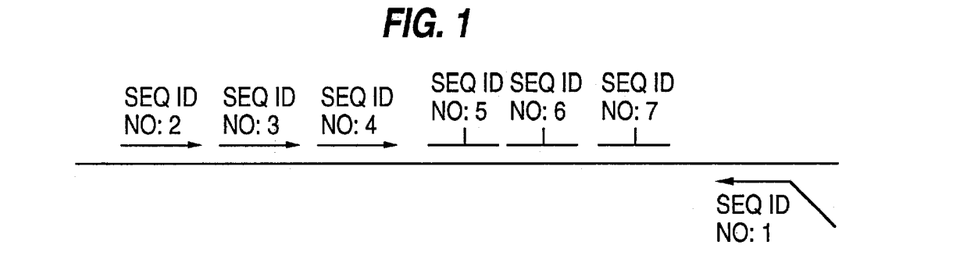
FIG. 1 shows a positional relation among the first primer for amplification, the second primer for amplification, detecting probe and capturing probe.

FIG. 1 shows the positional relation of the target nucleic acid sequence ($\beta$2.7 gene of the CMV nucleic acid) with the base sequences mentioned in SEQ ID NO:1 to NO:7 of the Sequence Listing.

The first primer for the CMV amplification used in the present invention has a nucleic acid sequence which is sufficiently complementary to the target nucleic acid sequence and a promoter sequence to the side of its 5'-terminal.

Further, the second primer for the CMV amplification is a nucleic acid sequence which is sufficiently homologous to the target nucleic acid sequence and its 3'-terminal is directed to the 3'-terminal of the first primer on the complementary chain.

Capturing probe or detecting probe is established in such a manner that it is capable of hybridizing with the amplified product of any combination of the first and the second primers for the CMV amplification.

The primer for amplifying the CMV in accordance with the present invention may be deoxyribonucleic acid (DNA) and can be prepared by means of chemical synthesis. For example, it can be synthesized by a phosphoamidite method using a DNA synthesizer (type 391) of Perkin-Elmer. Deblocking of various oligonucleotides is carried out by aqueous ammonia. Purification may be carried out by means of an FPLC using a reverse phase column. Examples of other synthetic methods are phosphoric acid triester method, H-phosphonate method and thiophosphite method. When the target nucleic acid sequence has a variation or when the object is a common amplification with other amplifying domain or with other similar virus, there may be a point mutation such as deletion, insertion and substitution in the primer.

The primer of the present invention is a synthetic substance and, therefore, it is possible to prepare an oligonucleotide of a constant quality in an easy manner and also in large quantities.

There is no particular limitation for the promoter sequence of the first primer for CMV amplification used in the present invention but it is necessary to function so that the DNA-dependent RNA polymerase does act. With respect to such a promoter sequence, (SEQ ID NO:8) 5'-AAT TCT AAT ACG ACT CAC TAT AGG G-3' has been known in the case of, for example, T7 RNA polymerase.

In addition, the promoter sequence may contain a spacer until the initiating point for the amplification. For example, a part of a sequence such as 5'-AGG A-3' may be bound to the 3'-terminal of the promoter sequence.

Examples of other promoter sequences (SEQ ID NOS: 9 and 10, respectively) are as follows.

5'-ATT AAC CCT CAC TAA AG-3' for T3 RNA polymerase; and

5'-ATT TAG GTG ACA CTA TA-3' for SP6 RNA polymerase.

Further, the second primer for CMV amplification in the present invention has a nucleic acid sequence which is complementary to the nucleic acid sequence of the elongated first primer and is sufficiently homologous to the target nucleic acid sequence. In addition to the supplementary nucleic acid sequence to the elongated first primer, the second primer may have a promoter sequence to the side of its 5'-terminal if necessary.

When the second primer has a promoter sequence, it may be same as or different from the promoter sequence of the first primer. When it is different, plural DNA-dependent RNA polymerases acting on each of the promoters may be used if necessary. For example, when T7 promoter, T3 promoter or SP6 promoter is used as the promoter sequence of the second primer, then T7 RNA polymerase, T3 RNA polymerase or SP6 RNA polymerase is used, respectively.

With respect to the DNA-dependent RNA polymerases and the concomitant promoter sequences, the above-mentioned three types are preferred although they are not limited thereto. It is particularly preferred to use T7 RNA polymerase and its promoter sequence.

It is more preferred that, when the second primer has a promoter sequence, both the first and the second primers are bound with a promoter sequence of T7 RNA polymerase whereby copy numbers are increased by the T7 RNA polymerase.

The domain where the hybridization takes place with target nucleic acid sequences or complementary sequences of the first and the second primers or the elongated primers requires a nucleic acid sequence consisting of at least fifteen bases of each of the sequences of the Sequence Listing.

According to the paper by Fahy et al. (PCR Methods and Applications, 1991; l:p.25–33), the use of the bases from 15 to 30 is reported to be preferred in a 3SR method which is a similar technique as an NASBA method. Accordingly, depending upon a method for preparing a target nucleic acid sequence and also a method for amplifying using an RNA polymerase, an optimum sequence and optimum sequence length may be selected from 15 to 30 bases. Preferably, the sequence at the side of the 3'-terminal is a nucleic acid sequence consisting of at least 15 continuous bases of the sequence as shown in the Sequence Listing. The ideal length of the domain where hybridization takes place is preferably from 15 bases to the whole sequence length as shown in the Sequence Listing, more preferably the whole sequence length.

In the present invention, the following combinations are available as primers for amplification.

TABLE 1

| First Primer for Amplification | Second Primer for Amplification |
|---|---|
| SEQ ID NO:1 + Promoter Sequence | SEQ ID NO:2, NO:3 or NO:4 + Promoter Sequence |
| SEQ ID NO:1 + Promoter Sequence | SEQ ID NO:2, NO:3 or NO:4 |
| SEQ ID NO:2, NO:3 or NO:4 | SEQ ID NO:1 + Promoter Sequence |

The RNA-dependent DNA polymerase (a reverse transcriptase) used in the present invention is an enzyme which synthesizes DNA from oligodeoxyribonucleotide primer and RNA template. In addition, this enzyme may contain DNA-dependent DNA polymerase (DNA polymerase) and ribonuclease H (RNase H) activity. Examples of such an enzyme are those derived from other retrovirus such as avian myoblast virus polymerase (AMV reverse transcriptase) and Maloney mouse leukemia virus.

With respect to the thermostable RNA-dependent DNA polymerase (reverse transcriptase), it has been also known that the DNA- dependent DNA polymerases derived from *Thermus thermophilus* and from *Thermus aquaticus* exhibit said enzymatic activity.

The ribonuclease H (RNase H) used in the present invention is an enzyme capable of hydrolyzing the RNA which is annealed to a complementary DNA. This enzyme should not be able to hydrolyze the single-stranded or double-stranded RNA or all DNA. Examples of the preferred enzyme are RNase H derived from *Escherichia coli* and RNase H derived from bovine thymus. Examples of the thermostable RNase H are RNase H derived from *Thermus thermophilus*. It has also been found that the DNA-dependent DNA polymerase derived from *Thermus thermophilus* has an RNase H activity too and, when said enzyme is used, it is now possible to utilize three kinds of enzymatic activity by the use of a single substance (enzyme) instead of the use of thermostable RNA-dependent DNA polymerase (reverse transcriptase) and thermostable RNase H.

The DNA-dependent DNA polymerase (DNA polymerase) used in the present invention is an enzyme which is capable of synthesizing DNA from oligodeoxyribonucleotide primer and a DNA template. Examples of such an enzyme are AMV reverse transcriptase, DNA polymerase isolated from tissues of mammals such as bovine thymus, Klenow fragment of DNA polymerase I derived from *Escherichia coli* and DNA polymerase derived from bacteriophage T7.

Other examples are the DNA polymerases derived from *Thermus thermophilus, Thermus aquaticus, Pyrococcus furiosus* and *Thermococcus litoralis*.

The DNA-dependent RNA polymerase (RNA polymerase) used in the present invention is an enzyme which binds to a promoter sequence and is capable of specifically initiating the synthesis of RNA at the initiation site regulated at near this promoter sequence. Said enzyme is capable of synthesizing several RNA copies per copy which is functional to the template within a suitable time. Examples of the suitable enzyme are other bacteriophage RNA polymerases such as bacteriophage T7 RNA polymerase, phage T3, phage XII, Salmonella phage sp6 or Pseudomonas phage gh-1. In addition, the RNA polymerases derived from other procaryotic and eucaryotic cells may be used too.

It has been for example known that the DNA polymerases derived from *Thermus thermophilus* and *Thermus aguaticus* have an RNA polymerase activity and one kind of DNA polymerase having both activities may be used commonly as well.

In carrying out an NASBA method using the present invention, it may be done by referring, for example, to a literature (J. Virol. Methods 35:273–286). An example is that, in a reaction mixture of 25 μl, an arrangement is conducted so as to make the final concentrations after addition of the enzyme as follows. Thus, 40 mM of Tris (pH 8.5); 20 mM of magnesium chloride; 40 mM of potassium chloride; 5 mM of DTT; 15% of DMSO; lmM of dNTP; 4.1 mM of rNTP; 0.2 μM of the first primer; and 0.2 μM of the second primer. Then the reaction mixture is mixed with the extracted RNA and heated at 65° C. for five minutes. After that, 2.5 μg of BSA, 12 U of RNA Guard, 20 U of T7 RNA polymerase, 4U of AMV reverse transcriptase and 0.2 U of ribonuclease H (RNase H) derived from *Escherichia coli* are added to make 25 μl followed by incubating for three hours. Under this amplifying condition, there may be a case where modification of the sequence of the primer is necessary depending upon the extracting method of the target nucleic acid and also upon the conditions upon the extraction. In that case, concentrations of DMSO, rNTP, etc. in the above-mentioned condition may be optimized.

In the detecting probe or capturing probe used in the present invention, a nucleic acid sequence consisting of at least fifteen continuous bases as shown in SEQ ID NO:5, NO:6 or NO:7 of the Sequence Listing is necessary.

Like the primer for amplification, the detecting probe or the capturing probe may be deoxyribonucleic acid (DNA) and can be prepared by a chemical synthesis. For example, it can be synthesized by a phosphoamidite method using a DNA synthesizer (type 391) of Perkin-Elmer. Deblocking is carried by aqueous ammonia. Purification may be carried out by means of an FPLC using an MONO-Q column or a reversed phase column. Examples of other synthetic methods are phosphoric acid triester method, H-phosphonate method and thiophosphite method.

Moreover, in synthesizing the oligonucleotide, oligo dCTP, oligo dTTP, oligo DATP, oligo dGTP or nucleotide having fluorescence substance, linker arm, biotin, etc. may be added to 5'-terminal or to 3'-terminal.

Alternatively, the synthesis may be conducted by substituting nucleotide having fluorescence substance, linker arm, biotin, etc. for the nucleotide in the oligonucleotide. Further, known labels such as radioactive substances, enzymes or fluorescence substances may be introduced into the synthesized nucleotide.

Examples of such a labeling method when oligonucleotide is labeled with an enzyme are that the nucleotide having a linker arm is chemically synthesized from deoxyuridine to substitute or add as one member of the oligonucleotide (Japanese Laid-Open Patent Publication Sho-60/500,717) and alkaline phosphatase or peroxidase is bound to the linker (Nucleic Acids Research; volume 14, page 6115, 1986). When there is a variation in the target nucleic acid sequence and the amplified product, a point mutation such as deletion, insertion or substitution may be present in the probe.

It is necessary that the detecting probe of the present invention is modified by a label such as enzyme, biotin, fluorescence substance or radioactive substance or by a substance capable of binding said label by means of the above-mentioned method. And a detection operation may be carried out using the nature of the respective label.

In one detection method, the amplified product from the target nucleic acid derived from CMV is subjected to an electrophoresis using agarose gel, then nucleic acid is immobilized to the membrane by a Southern blotting and subjected to a hybridization with a detecting probe labeled whereupon a detecting operation depending upon the nature of the label may be carried out. Alternatively, a detection operation may be conducted by the above-mentioned method after immobilizing the amplified product as it is on the membrane followed by modifying by an alkali.

Another detecting method is a sandwich technique using detecting probe and capturing probe. As mentioned already, it is necessary that the detecting probe is labeled by such as enzyme, biotin, fluorescence substance or radioactive substance or by a substance capable of binding with said label. Although the capturing probe may be left unmodified when adsorbed with a support, it may be added with or substituted by a nucleotide having biotin, linker arm, fluorescence substance, etc. or added with oligo dGTP, oligo DATP, oligo dTTP, oligo dCTP, etc. depending upon the nature of the support.

Examples of the practical methods applicable are a liquid phase sandwich technique in which target nucleic acid, detecting probe and capturing probe, in a liquid phase, with a capturing probe which is modified so as to make the capturing possible and then this modified capturing probe is captured by a capture which is fixed to the support (Japanese Laid-Open Patent Publications Sho-61/195699, Sho-61/274699, Sho-62/229068, Hei-01/104200, Hei-01/501399, etc.); a solid phase sandwich technique in which a capturing probe directly fixed to the support and a detecting probe modified by a label or a substance capable of binding with a label (Japanese Laid-Open Patent Publications Sho-60/188100, Sho-60/188397, Sho-61/264240, Sho-62/851564, etc.); and the like.

Particularly preferably, a capturing probe containing a linker arm is immobilized in a solid phase (Japanese Laid-Open Patent Publication Hei-06/329694) and the amplified product is hybridized with a detecting probe whereby the detection may be performed.

Advantages of the Inventions

As a result of the use of the amplifying primer of the present invention which is suitable for an NASBA method and the detecting and capturing probes which are to judge the amplified product obtained by said primer, it is now possible to solve the problems in the conventional clinical test methods for CMV and to detect the CMV in an easy, rapid and specific manner and also with a high sensitivity.

EXAMPLES

The present invention will now be further illustrated by way of the following examples.

Example 1.

(Synthesis of primers)

A phosphoamidite method was carried out using a DNA synthesizer type 391 (manufactured by ABI) whereupon the first primer (SEQ ID NO:1) having a sequence shown in the Sequence Listing (i.e. a sequence which is complementary to mRNA of cytomegalovirus wherein the promoter sequence of T7 RNA polymerase is bound at 5'-terminal) and the second primers (SEQ ID NO:2, NO:3 and NO:4) having a sequence which is homologous to mRNA of cytomegalovirus were synthesized. The specific means in accordance with the Manual of ABI was conducted in a scale of 0.2M. Deblocking of various oligonucleotides was carried out with an aqueous ammonia for overnight at 55° C. Purification was carried out by means of an FPLC (manufactured by Pharmacia) using a reversed phase column.

(Preparation of RNA from an infected cells CMV)

According to a method by Boom et al. (J. Clin. Microbiol. 28:495–503), RNA was prepared from the cells infected with CMV (AD 169 strain). Thus, cultured cell liquid was treated in a buffer for dissolution containing Triton X-100 (polyoxethylene (10) octylphenyl ether) and guanidium thiocyanate (GuSCN) and silica particle was added thereto to adsorb mRNA therewith. The mRNA-adsorbed silica particle was washed twice with a wash buffer containing GuSCN, twice with 70% ethanol and once with acetone and the residue was dried. Elution was carried out using distilled water containing neither ribonuclease (RNase) nor deoxyribonuclease (DNase). The eluate was subjected to a gradient dilution with the same distilled water.

(Preparation of a Detecting Probe)

(1) Synthesis of CMV-Detecting Oligonucleotide having Linker Arm.

Nucleic acid sequences shown in the Sequence Listing, i.e. the detecting probes (SEQ ID NO:5, NO:6 and NO:7), were synthesized by a phosphoamidite method using a synthesizer (type 391 manufactured by Perkin-Elmer). At that time, a DNA synthetic method mentioned in the Japanese Laid-Open Patent Publication Sho-60/500717 was conducted whereby the uridine having a linker arm at 5'-position and chemically synthesized from deoxyuridine was introduced into the above-mentioned oligonucleotide. This uridine can be substituted with any T in the oligonucleotide but, in this Example, it was bound at a 5'-terminal. Deblocking of the synthesized linker oligonucleotide was carried out at 55° C. for overnight using an aqueous ammonia. Purification was carried out by means of an FPLC (manufactured by Pharmacia) using a reversed phase column.

(2) Labeling of Linker Oligonucleotide with Alkaline Phosphatase.

An alkaline phosphatase was bound via a linker site of the above-mentioned linker oligonucleotide according to a method of a literature (Nucleic Acids Research, vol. 14, p. 6114, 1986). The linker oligonucleotide 1.5 $A_{260}$ was dissolved in 12.5 μl of 0.2 M sodium bicarbonate, 25 μl of 10 mg succinimidyl suberate (DSS) was added thereto and a reaction was performed at room temperature for two minutes. The reaction solution was subjected to a gel filtration using a column of Sephadex G-25 equilibrated with 1 mM sodium acetate (pH: 5.0) to remove an excess of DSS.

The linker oligonucleotide wherein the terminal amino group was activated was further made to react at room temperature for 16 hours with an alkaline phosphatase (being dissolved in 100 mM of sodium bicarbonate and 3M of HCl) in a 2-fold amount in terms of molar ratio to give a probe labeled with an alkaline phosphatase. The resulting labeled probe was purified by means of an FPLC (manufactured by Pharmacia) using a column of an anionic exchange resin and the fractions containing the purified labeled probe were collected and concentrated by means of an ultrafiltration using Centricon 30 K (Amicon).

(Amplification Reaction) The amplification reaction was carried out according to a literature (J. Virol. Methods 35:273–286). Thus, in a reaction system of 25 μl, an arrangement was done so as to make the final concentrations after addition of the enzyme as follows. Thus, 40 mM of Tris (pH 8.5); 20 mM of magnesium chloride; 40 mM of potassium chloride; 5 mM of DTT; 15% of DMSO; 1 mM of dNTP; 4.1 mM of rNTP; 0.2 μM of the first primer; and 0.2 μM of the second primer. Then it was mixed with the extracted RNA followed by heating at 65° C. for five minutes. Then 2.5 μg of BSA, 12 U of RNA Guard, 20 U of T7 RNA polymerase, 4 U of AMV reverse transcriptase and 0.2 U of ribonuclease H (RNase H) were added to make the total volume 25 μl followed by incubating for three hours.

(Detection) The reaction solution (1 μl) was dropped onto a nylon membrane and the nucleic acid was immobilized under an alkaline condition. This membrane was neutralized and immobilized under an alkaline condition. After this membrane was neutralized, it was transferred to a hybridization bag, a hybridization buffer (5×SSC; 0.5% of BSA, 0.5% of PVP and 1% of SDS) containing the above-mentioned nucleic acid probe labeled with an alkaline phosphatase and a hybridization was carried out at 50° C. for 15 minutes. The nylon membrane was taken out from the hybridization bag and subjected to an osmotic washing with a detergent solution 1 (1×SSC; 1% of SDS) at 50° C. for ten minutes. This was further subjected to an osmotic washing with a detergent solution 2 (1×SSC) at room temperature for ten minutes. The membrane was transferred to a new hybridization back, a substrate solution (0.1 M of Tris, 0.1M of sodium chloride, 0.1M of magnesium chloride, 0.3 M of magnesium chloride, nitroblue tetrazolium, and 0.3 mg/ml of bromochlorophenyl phosphate; pH 7.5) was added thereto and the mixture was sealed and incubated at 37° C. for 30 minutes.

(Results)

Figure 2:
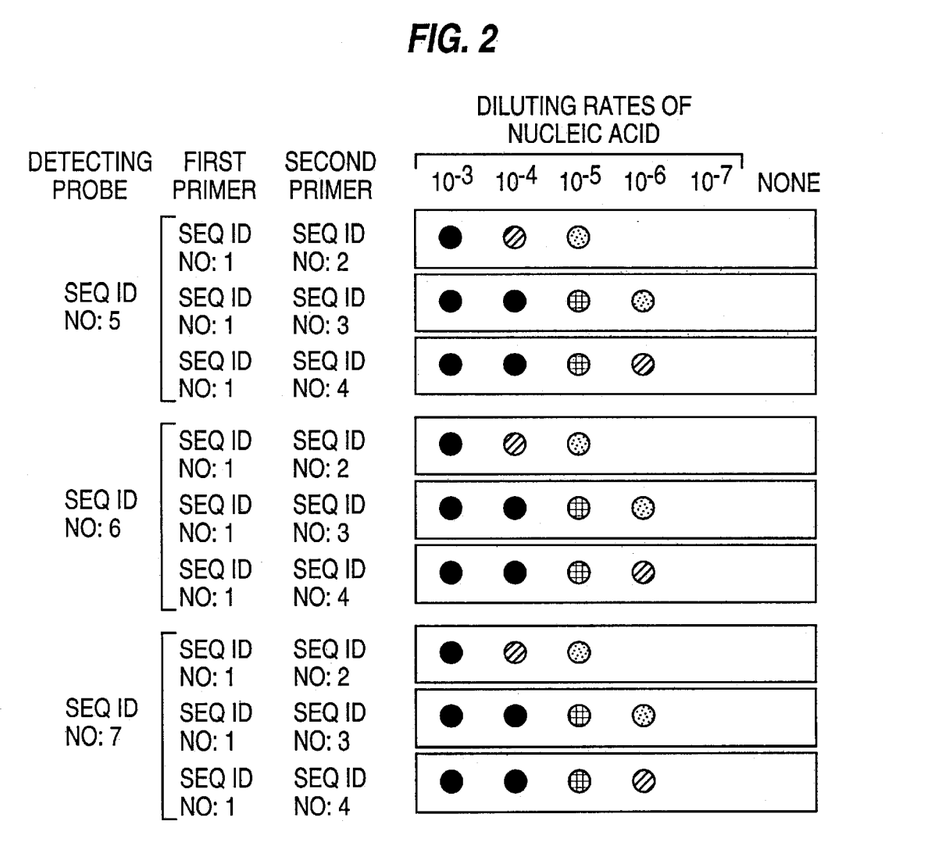
FIG. 2 shows the result of investigation on the combination of each of the primers with each of the probes.

Results of the investigation on the combination of each of the primers with each of the probes are given in FIG. 2. The detection sensitivity was the highest when the sequence of SEQ ID NO:1 of the Sequence Listing was used as the first primer and that of SEQ ID NO:3 or NO:4 of the Sequence Listing was used as the second primer. When the sequence of SEQ ID NO:2 of the Sequence Listing was used as the second primer, the detection sensitivity was low but, in the detection of CMV, there are some cases where a low sensitivity is preferred depending upon the condition of a disease. Accordingly, an optimum combination is to be selected depending upon the necessary detection sensitivity.

Example 2.

(Synthesis of Primers)

The first primer (SEQ ID NO:1) having a sequence given in the Sequence Listing, i.e. a sequence complementary to mRNA of cytomegalovirus binding a promoter sequence (AAT TCT AAT ACG ACT CAC TAT AGG GAG GA), SEQ ID NO: 11 of T7 RNA polymerase at the 5'-terminal and the second primer (SEQ ID NO:4) having a sequence homologous to mRNA of cytomegalovirus were synthesized by a phosphoamidite method using a DNA synthesizer (type 391) manufactured by Perkin-Elmer. Specific means were performed in accordance with the instruction manual of the Perkin-Elmer and were done in a 0.2 M scale. Deblocking of various oligonucleotides was carried out at 55° C for overnight using an aqueous ammonia. Purification was carried out by means of an FPLC (manufactured by Pharmacia) using a reversed phase column.

(Synthesis of Capturing Probe)

Sequences shown in the Sequence Listing, i.e. capturing probes (SEQ ID NO:5, NO:6 and NO:7), were prepared by a phosphoamidite method using a DNA synthesizer (model 391) manufactured by Perkin-Elmer. In that synthesis, uridine having a linker arm at 5-position and chemically synthesized from deoxyuridine was introduced into the above-mentioned oligonucleotide according to a synthetic method mentioned in the Japanese Laid-Open Patent Publication Sho- 60/500717. This uridine can be substituted with any T in the oligonucleotide and, in this Example, it was bound at the 5'-terminal. Deblocking of the synthesized linker oligonucleotide was carried out at 55° C. for overnight using an aqueous ammonia. Purification was performed by means of an FPLC (manufactured by Pharmacia) using a reversed phase column.

(Binding of Capturing Probe with Solid Phase Support)

A microtiter plate made of polystyrene (Microlite 2 manufactured by Dynatec) was used as a solid phase support. The capturing probe was diluted to an extent of 10 pmoles/ml using 50 mM borate buffer. Each 100 μl of the solution was placed on a well of the microtiter plate and incubated at room temperature for one night. The capturing probe solution was removed from the resulting plate using an aspirator and, in order to prevent a nonspecific binding, each 150 μl of block buffer was placed followed by allowing to stand at room temperature for two hours for blocking.

(Amplification Reaction)

As to the target nucleic acid, the 1000-fold diluted solution of the gradient diluted solution of nucleic acid used in Example 1 was used. The target nucleic acid was subjected to an amplification reaction by the same manner as in Example 1.

(Detection by Means of a Sandwich Hybridization Technique) The resulting amplified product was denatured with an equivalent amount of 0.6N NaOH at room temperature for one minute. A block buffer was removed from a plate which was fixed with a capturing probe and 10 μl of the denatured sample was added thereto. Then 100 μl of a hybridization buffer was added and a hybridization was carried out at 50° C. for 60 minutes. The solution was removed from the well and washed with 200 1 of a detergent solution 1 (2×SSC; 1% of sodium laurylsulfate) at 50° C. for five minutes. Then the detergent solution 1 was removed, the inside of the well was rinsed with 200 μl of 1×SSC, then 100 μl of a probe solution labeled with an alkaline phosphatase was added and a hybridization was carried out at 50° C. for 60 minutes. The probe solution was removed from the well, 200 μl of the detergent solution 1 was added, washing was performed at 50° C. for ten minutes, then 200 μl of detergent solution 2 (1×SSC; 0.5% of Triton X-100) was added and a washing was carried out at room temperature for ten minutes. Finally, the inside of the well was rinsed with 200 μl of 1×SSC, 100 1 of Lumiphos 480 (manufactured by Wako Pure Chemicals; a chemiluminescence substance which is a substrate for an alkaline phosphatase) was added and a luminescence reaction was conducted in a dark place at 37° C. for 15 minutes. The luminescent amount was measured by a Microlite 1000 (manufactured by Dynatec).

(Effects) Combinations of each of the detecting probes with each of the capturing probes were investigated (Table 2). Although there were some differences in the detected amounts among the combinations, the amplified product was able to be detected in all of the combinations. The highest detection sensitivity was achieved in the case where SEQ ID NO:5 was a capturing probe and SEQ ID NO:7 was a detecting probe. In a detecting system where a low detecting amount is necessary, combinations giving low detecting values are to be applied. In other words, a combination which is optimum to the necessary detecting sensitivity is to be chosen.

TABLE 2

| Detecting Probe | SEQ ID NO:5 | | SEQ ID NO:6 | | SEQ ID NO:7 | |
| --- | --- | --- | --- | --- | --- | --- |
| Capturing Probe | SEQ ID NO:6 | SEQ ID NO:7 | SEQ ID NO:5 | SEQ ID NO:7 | SEQ ID NO:5 | SEQ ID NO:6 |
| Noise | 1.2 | 1.2 | 1.0 | 1.0 | 1.1 | 1.1 |
| Signal | 8.3 | 39.8 | 17.8 | 13.0 | 61.8 | 9.3 (kcps) |

What is claimed is:

1. An oligonucleotide for amplifying a nucleic acid of cytomegalovirus (CMV) utilizing a nucleic acid sequence (β2.7), said oligonucleotide containing a nucleic acid sequence consisting of at least fifteen continuous bases selected from the nucleic acid sequence of SEQ ID NO:1.

2. An oligonucleotide for amplifying a nucleic acid of cytomegalovirus (CMV) utilizing a nucleic acid sequence (β2.7), said oligonucleotide containing a nucleic acid sequence comprising at least fifteen continuous bases selected from the nucleic acid sequence of SEQ ID NO:2 [NO;3, or NO:4] SEQ ID NO:3, or SEQ ID NO:4.

3. An oligonucleotide for amplifying a nucleic acid of cytomegalovirus (CMV) utilizing a nucleic acid sequence (β2.7), said oligonucleotide linking a promoter sequence of DNA-dependent RNA polymerase at the 5'-terminal of oligonucleotide of claim 1.

4. A kit for amplifying a nucleic acid of cytomegalovirus (CMV), comprising:
   (a) a first primer for amplifying a nucleic acid of cytomegalovirus (CMV) which first primer contains a nucleic acid sequence comprising at least fifteen continuous bases selected from the nucleic acid sequence of SEQ ID NO:1 and has a promoter sequence of a DNA-dependent RNA polymerase at the 5'-terminal,
   (b) a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4,
   (c) a substance having an RNA-dependent DNA polymerase activity,
   (d) a substance having a ribonuclease H activity,
   (e) a substance having a DNA-dependent DNA polymerase activity,
   (f) a substance having a DNA-dependent RNA polymerase activity,
   (g) ribonucleoside triphosphates and
   (h) deoxyribonucleoside triphosphates.

5. A kit for amplifying a nucleic acid of cytomegalovirus (CMV), comprising:
   (a) a first primer for amplifying a nucleic acid of cytomegalovirus (CMV) which first primer contains a nucleic acid sequence comprising at least fifteen continuous bases selected from the nucleic acid sequence of SEQ ID NO:2, SEQ ID NO:3, OR SEQ ID NO:4. and has a promoter sequence of a DNA-dependent RNA polymerase at the 5'-terminal,
   (b) a second primer for amplifying a nucleic acid of cytomegalovirus (CMV) which second primer contains a nucleic acid sequence comprising at least fifteen continuous bases selected from the nucleic acid sequence of SEQ ID NO:1,
   (c) a substance having an RNA-dependent DNA polymerase activity,
   (d) a substance having a ribonuclease H activity,
   (e) a substance having a DNA-dependent DNA polymerase activity,
   (f) a substance having a DNA-dependent RNA polymerase activity,
   (g) ribonucleoside triphosphates and
   (h) deoxyribonucleoside triphosphates.

6. A kit for amplifying a nucleic acid of cytomegalovirus (CMV), comprising:
   (a) a first primer for amplifying a nucleic acid of cytomegalovirus (CMV) which firt primer contains a nucleic acid sequence comprising at least fifteen continuous bases selected from the nucleic acid sequence of SEQ ID NO:1 and has a promoter sequence of a DNA-dependent RNA polymerase at the 5'-terminal,
   (b) a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4, and has a promoter sequence of a DNA-dependent RNA polymerase at the 5'-terminal,
   (c) a substance having an RNA-dependent DNA polymerase activity,
   (d) a substance having a ribonuclease H activity,
   (e) a substance having a DNA-dependent DNA polymerase activity,
   (f) a substance having a DNA-dependent RNA polymerase activity,
   (g) ribonucleoside triphosphates and
   (h) deoxyribonucleoside triphosphates.

7. A method for amplifying a nucleic acid of cytomegalovirus (CMV) utilizing a nucleic acid sequence ($\mu$2.7), which method comprises
   (a) Providing a target nucleic acid consisting of RNA (+);
   (b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:1 and has a promoter sequence of a DNA-dependent RNA polymerase at the 5'-terminal with the RNA (+) as a template to elongate the primer by the RNA-dependent DNA polymerase, whereupon an elongated RNA/DNA hybrid is obtained,
   (c) digesting the RNA in the elongated RNA/DNA hybrid by a ribonuclease H which specially digests only the RNA of the elongated RNA/DNA hybrids whereupon a single-stranded DNA is obtained,
   (d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4, with the single-stranded DNA as a template to perform a DNA elongation reaction by a DNA-dependent DNA polymerase,_ whereupon a double-stranded DNA intermediate having a functional promoter sequence upstream of the 5'-terminal is produced,
   (e) transcribing a single-stranded RNA (-) increasingly from the double-stranded DNA intermediate by the DNA-dependent RNA polymerase which is capable of recognizing the functional promoter sequence of step (d),
   (f) hybridizing the second primer for amplifying a nucleic acid of cytomegalovirus (CMV) with the single stranded RNA (-) obtained in step (e) as a template to perform a DNA elongation reaction by a RNA-dependent DNA polymerase, whereupon an elongated RNA/DNA hybrid is obtained,
   (g) digesting the RNA in the elongated RNA/DNA hybrid by a ribonuclease H which specially digests only the RNA of the elongated RNA/DNA hybrids whereupon a single-stranded DNA is obtained, (h) hybridizing the first primer for amplifying a nucleic acid of cytomegalovirus (CMV) with the single-stranded DNA as a template to perform a DNA elongation reaction by a DNA-dependent DNA polymerase, whereupon a double-stranded DNA intermediate having a functional promoter sequence upstream of the 5'-terminal is produced, (i) transcribing the single-stranded RNA (-) increasingly from the double-stranded DNA intermediate by the DNA-dependent RNA polymerase which is capable of recognizing the functional promoter sequence of step (h), and (j) optionally, repeating steps (f) to (i) using the resulting single stranded RNA (-) as a template in optionally repeated step (f).

8. A method for amplifying a nucleic acid of cytomegalovirus (CMV) utilizing a nucleic acid sequence ($\mu$2.7), which method comprises:

(a) providing a target nucleic acid consisting of RNA (+);

(b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:1, and has a promoter sequence of a DNA-dependent RNA polymerase at the 5'-terminal with the RNA (+) as a template to elongate the primer by the RNA-dependent DNA polymerase, whereupon an elongated RNA/DNA hybrid is obtained, (c) digesting the RNA in the elongated RNA/DNA hybrid by a ribonuclease H which specially digests only the RNA of the elongated RNA/DNA hybrid, whereupon a single-stranded DNA is obtained, (d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4, and has a promoter sequence of a DNA-dependent RNA polymerase at the 5'-terminal with the single-stranded DNA as a template to perform a DNA elongation reaction by a DNA-dependent DNA polymerase whereupon a double-stranded DNA intermediate having a functional promoter sequence upstream of the 5'-terminal is produced, (e) transcribing a single-stranded RNA (-) increasingly from the double-stranded DNA intermediate by the DNA-dependent RNA polymerase which is capable of recognizing the functional promoter sequence of step (d), (f) hybridizing the second primer for amplifying a nucleic acid of cytomegalovirus (CMV) with the single stranded RNA (-) obtained in step (e) as a template to perform a DNA elongation reaction by a RNA-dependent DNA polymerase, whereupon an elongated RNA/DNA hybrid is obtained, (g) digesting the RNA in the elongated RNA/DNA hybrid by a ribonuclease H which specially digests only the RNA of the elongated RNA/DNA hybrid, whereupon a single-stranded DNA is obtained, (h) hybridizing the first primer for amplifying a nucleic acid of cytomegalovirus (CMV) with the single-stranded DNA as a template to perform a DNA elongation reaction by a DNA-dependent DNA polymerase, whereupon a double-stranded DNA intermediate having a functional promoter sequence upstream of both terminals is produced, (i) transcribing the single-stranded RNA(-) and RNA(+) increasingly from the double-stranded DNA intermediate by the DNA-dependent RNA polymerase which is capable of recognizing the functional promoter sequence of step (h), and (j) optionally, repeating steps (f) to (i) using the resulting single stranded RNA(-) and RNA(+) as a template in optionally repeated step (f).

9. A probe for detecting and/or capturing a nucleic acid of the cytomegalovirus (CMV), said probe containing a nucleic acid sequence comprising at least fifteen continuous bases selected from the nucleic acid sequence of SEQ ID NO:5, SEQ ID NO:6, and/or SEQ ID NO:7, or a complementary nucleic acid thereof, wherein the nucleic acid sequence optionally may be modified.

10. A kit for detecting and/or capturing a nucleic acid of the cytomegalovirus (CMV), comprising:

(a) a first primer for amplifying a nucleic acid of cytomegalovirus (CMV) which first primer contains a nucleic acid sequence comprising at least fifteen continuous bases selected from the nucleic acid sequence of SEQ ID NO:1 and has a promoter sequence of a DNA-dependent RNA polymerase at the 5'-terminal, (b) a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4, (c) a substance having an RNA-dependent DNA polymerase activity, (d) a substance having a ribonuclease H activity.

(e) a substance having a DNA-dependent DNA polymerase activity.

(f) a substance having a DNA-dependent RNA polymerase activity, (g) ribonucleoside triphosphates, (h) deoxyribonucleoside triphosphates and (i) a probe for detecting and/or capturing a nucleic acid of the cytomegalovirus (CMV) which probe contains a nucleic acid sequence comprising at least fifteen continuous bases selected from the nucleic acid sequence of SEQ ID NO:5, SEQ ID NO:6, and/or SEQ ID NO:7, or a complementary nucleic acid thereof, wherein the nucleic acid sequence optionally may be modified.

11. A method for detecting and/or capturing a nucleic acid of the cytomegalovirus (CMV) utilizing a nucleic acid sequence ($\mu$2.7), which comprises:

(a) providing a target nucleic acid consisting of RNA (+);

(b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:1 and has a promoter sequence of a DNA-dependent RNA polymerase at the 5'-terminal with the RNA (+) as a template to elongate the primer by the RNA-dependent DNA polymerase, whereupon an elongated RNA/DNA hybrid is obtained, (c) digesting the RNA in the elongated RNA/DNA hybrid by a ribonuclease H which specially digests only the RNA of the elongated RNA/DNA hybrid. whereupon a single-stranded DNA is obtained, (d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4, with the single-stranded DNA as a template to perform a DNA elongation reaction by a DNA-dependent DNA polymerase, whereupon a double-stranded DNA intermediate having a functional promoter sequence upstream of the 5'-terminal is produced, (e) transcribing a single-stranded RNA (-) increasingly from the double-stranded DNA intermediate by the DNA-dependent RNA polymerase which is capable of recognizing the functional promoter sequence of step (d), (f) hybridizing the second primer for amplifying a nucleic acid of cytomegalovirus (CMV) with the single stranded RNA (-) obtained in the above step (e) as a template to perform a DNA elongation reaction by a RNA-dependent DNA polymerase, whereupon an elongated RNA/DNA hybrid is obtained, (g) digesting the RNA in the elongated RNA/DNA hybrid by a ribonuclease H which specially digests only the RNA of the elongated RNA/DNA hybrid, whereupon a single-stranded DNA is obtained, (h) hybridizing the first Primer for amplifying a nucleic acid of cytomegalovirus (CMV) with the single-stranded DNA as a template to perform a DNA elongation reaction by a DNA-dependent DNA polymerase, whereupon a double-stranded DNA intermediate having a functional promoter sequence upstream of the 5'-terminal is produced, (i) transcribing the single-stranded RNA (-) increasingly from the double-stranded DNA intermediate by the DNA-dependent RNA polymerase which is capable of recognizing the functional promoter sequence of step (h).

(j) optionally. repeating steps (f) to (i) using the resulting single stranded RNA (-) as a template in optionally repeated step (f), and (k) detecting and/or capturing the resulting amplified nucleic acids with a probe for detecting and/or capturing a nucleic acid of the cytomegalovirus (CMV) which probe contains a nucleic acid sequence comprising at least fifteen continuous bases selected from the nucleic acid sequence of SEQ ID NO:5, SEQ ID NO:6, and/or SEQ ID NO:7, or a complementary nucleic acid thereof, wherein the nucleic acid sequence optionally may be modified by a label.

12. A method for detecting a nucleic acid of the cytomegalovirus (CMV) utilizing a nucleic acid sequence ($\mu$2.7), which method comprises (a) providing a target nucleic acid consisting of RNA (b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:1 and has a promoter sequence of a DNA-dependent RNA polymerase at the 5'-terminal with the RNA (+) as a template to elongate the primer by the RNA-dependent DNA polymerase. whereupon an elongated RNA/DNA hybrid is obtained, (c) digesting the RNA in the elongated RNA/DNA hybrid by a ribonuclease H which specially digests only the RNA of the elongated RNA/DNA hybrid, whereupon a single-stranded DNA is obtained, (d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4, with the single-stranded DNA as a template to perform a DNA elongation reaction by a DNA-dependent DNA polymerase, whereupon a double-stranded DNA intermediate having a functional promoter sequence upstream of the 5'-terminal is produced, (e) transcribing a single-stranded RNA (-) increasingly from the double-stranded DNA intermediate by the DNA-dependent RNA polymerase which is capable of recognizing the functional promoter sequence of step (d), (f) hybridizing the second primer for amplifying a nucleic acid of cytomegalovirus (CMV) with the single stranded RNA (-) obtained in step (e) as a template to perform a DNA elongation reaction by a RNA-dependent DNA polymerase. whereupon an elongated RNA/DNA hybrid is obtained.

(g) digesting the RNA in the elongated RNA/DNA hybrid by a ribonuclease H which specially digests only the RNA of the elongated RNA/DNA hybrid. whereupon a single-stranded DNA is obtained.

(h) hybridizing the first primer for amplifying a nucleic acid of cytomegalovirus (CMV) with the single-stranded DNA as a template to perform a DNA elongation reaction by a DNA-dependent DNA polymerase. whereupon a double-stranded DNA intermediate having a functional promoter sequence upstream of the 5'-terminal is produced, (i) transcribing the single-stranded RNA (-) increasingly from the double-stranded DNA intermediate by the DNA-dependent RNA polymerase which is capable of recognizing the functional promoter sequence of step (h), (j) optionally. repeating steps (f) to (i) using the resulting single stranded RNA (-) as a template in optionally repeated step (f).

(k) hybridizing the resulting nucleic acids with
  a capturing probe absorbed to or bound with a solid support which probe contains a nucleic acid sequence comprising at least fifteen continuous bases selected from the nucleic acid sequence of SEQ ID NO:5, SEQ ID NO:6, and/or SEQ ID NO:7, and which optionally may be modified and
  a detecting probe containing a nucleic acid sequence comprising at least fifteen continuous bases selected from the nucleic acid sequence of SEQ ID NO:5, SEQ ID NO:6, and/or SEQ ID NO:7, and which is modified by a labels separating any unreacted detecting probe, and (m) detecting the label of the optionally labeled capturing probe, the amplified nucleic acids and the detecting probe.

13. A kit for detecting and/or capturing a nucleic acid of the cytomegalovirus (CMV), comprising:

(a) a first primer for amplifying a nucleic acid of cytomegalovirus (CMV) which first primer contains a nucleic acid sequence comprising at least fifteen continuous bases selected from the nucleic acid sequence of SEQ ID NO:2, SEQ ID NO:3, OR SEQ ID NO:4, and has a promoter sequence of a DNA—dependent RNA polymerase at the 5'-terminal, (b) a second primer for amplifying a nucleic acid of cytomeqalovirus (CMV) which second primer contains a nucleic acid sequence comprising at least fifteen continuous bases selected from the nucleic acid sequence of SEQ ID NO:1.

(c) a substance having an RNA-dependent DNA polymerase activity, (d) a substance having a ribonuclease H activity, (e) a substance having a DNA-dependent DNA polymerase activity, (f) a substance having a DNA-dependent RNA polymerase activity, (g) ribonucleoside triphosphates, (h) deoxyribonucleoside triphosphates, and (i) a probe for detecting and/or capturing a nucleic acid of the cytomegalovirus (CMV) which probe contains a nucleic acid sequence comprising at least fifteen continuous bases selected from the nucleic acid sequence of SEQ ID NO:5, SEQ ID NO:6, and/or SEQ ID NO:7, or a complementary nucleic acid thereof, wherein the nucleic acid sequence optionally may be modified.

14. A kit for detecting and/or capturing a nucleic acid of the cytomegalovirus (CMV), comprising:

(a) a first primer for amplifying a nucleic acid of cytomegalovirus (CMV) which first primer contains a nucleic acid sequence comprising at least fifteen continuous bases selected from the nucleic acid sequence of SEQ ID NO:1 and has a promoter sequence of a DNA-dependent RNA polymerase at the 5'-terminal, (b) a second primer for amplifying a nucleic acid of cytomegalovirus (CMV) which secpond primer contains a nucleic acid sequence comprising at least fifteen continuous bases selected from the nucleic acid sequence of SEQ ID NO:2, SEQ ID NO:3, or SEQ ID NO:4, and has a promoter sequence of a DNA-dependent RNA polymerase at the 5'-terminal, (c) a substance having an RNA-dependent DNA polymerase activity, (d) a substance having a ribonuclease H activity, (e) a substance having a DNA-dependent DNA polymerase activity, (f) a substance having a DNA-dependent RNA polymerase activity, (g) ribonucleoside triphosphates and (h) deoxyribonucleoside triphosphates, and (i) a probe for detecting and/or capturing a nucleic acid of the cytomegalovirus (CMV) which probe contains a nucleic acid sequence comprising at least fifteen continuous bases selected from the nucleic acid sequence of SEQ ID NO:5, SEQ ID NO:6, and/or SEQ ID NO:7, or a complementary nucleic acid thereof, wherein the nucleic acid sequence optionally may be modified.

15. A method for detecting and/or capturing a nucleic acid of the cytomegalovirus (CMV) utilizing a nucleic acid sequence (β2.7), which comprises:

(a) providing a target nucleic acid consisting of RNA (+);

(b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:1, and has a promoter sequence of a DNA-dependent RNA polymerase at the 5'-terminal with the RNA (+) as a template to elongate the primer by the RNA-dependent DNA polymerase, whereupon an elongated RNAIDNA hybrid is obtained.

(c) digesting the RNA in the elongated RNA/DNA hybrid by a ribonuclease H which specially digests only the RNA of the elongated RNAIDNA hybrid. whereupon a single-stranded DNA is obtained.

(d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4, and has a promoter sequence of a DNA-dependent RNA polymerase at the 5'-terminal with the single-stranded DNA as a template to perform a DNA elongation reaction by a DNA-dependent DNA polymerase. whereupon a double-stranded DNA intermediate having a functional promoter sequence upstream of the 5'-terminal is produced, (e) transcribing a single-stranded RNA (-) increasingly from the double-stranded DNA intermediate by the DNA-dependent RNA Polymerase which is capable of recognizing the functional promoter sequence of step (d), (f) hybridizing the second primer for amplifying a nucleic acid of cytomegalovirus (CMV) with the single stranded RNA (-) obtained in step (e) as a template to perform a DNA elongation reaction by a RNA-dependent DNA polymerase, whereupon an elongated RNA/DNA hybrid is obtained, (g) digesting the RNA in the elongated RNA/DNA hybrid by a ribonuclease H which specially digests only the RNA of the elongated RNA/DNA hybrid, whereupon a single-stranded DNA is obtained, (h) hybridizing the first primer for amplifying a nucleic acid of cytomegalovirus (CMV) with the single-stranded DNA as a template to perform a DNA elongation reaction by a DNA-dependent DNA polymerase, whereupon a double-stranded DNA intermediate having a functional promoter sequence upstream of both terminals is produced, (i) transcribing the single-stranded RNA(-) and RNA(+) increasingly from the double-stranded DNA intermediate by the DNA-dependent RNA polymerase which is capable of recognizing the functional promoter sequence of step (h), and (j) optionally. repeating steps (f) to (i) using the resulting single stranded RNA(-) and RNA(+) as a template in optionally repeated step (f), and (k) detecting and/or capturing the resulting nucleic acids with a probe for detecting and/or capturing a nucleic acid of the cytomegalovirus (CMV) which probe contains a nucleic acid sequence comprising at least fifteen continuous bases selected from the nucleic acid sequence of SEQ ID NO:5, SEQ ID NO:6, and/or SEQ ID NO:7, or a complementary nucleic acid thereof, wherein the nucleic acid sequence optionally may be modified by a label.

16. A method for detecting a nucleic acid of the cytomegalovirus (CMV) utilizing a nucleic acid sequence (β2.7), which method comprises:

(a) providing a target nucleic acid consisting of RNA (b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:1, and has a promoter sequence of a DNA-dependent RNA polymerase at the 5'-terminal with the RNA (+) as a template to elongate the Primer by the RNA-dependent DNA polymerase, whereupon an elongated RNA/DNA hybrid is obtained, (c) digesting the RNA in the elongated RNA/DNA hybrid by a ribonuclease H which specially digests only the RNA of the elongated RNA/DNA hybrid, whereupon a single-stranded DNA is obtained.

(d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:2, SEQ ID NO:3, or SEQ ID NO:4, and has a promoter sequence of a DNA-dependent RNA polymerase at the 5'-terminal with the single-stranded DNA as a template to perform a DNA elongation reaction by a DNA-dependent DNA polymerase. whereupon a double-stranded DNA intermediate having a functional promoter sequence upstream of the 5'-terminal is produced.

(e) transcribing a single-stranded RNA (-) increasingly from the double-stranded DNA intermediate by the DNA-dependent RNA polymerase which is capable of recognizing the functional promoter sequence of step (d).

(f) hybridizing the second primer for amplifying a nucleic acid of cytomegalovirus (CMV) with the single stranded RNA (-) obtained in the above step (e) as a template to perform a DNA elongation reaction by a RNA-dependent DNA polymerase. whereupon an elongated RNA/DNA hybrid is obtained, (g) digesting the RNA in the elongated RNA/DNA hybrid by a ribonuclease H which specially digests only the RNA of the elongated RNA/DNA hybrid, whereupon a single-stranded DNA is obtained.

(h) hybridizing the first primer for amplifying a nucleic acid of cytomegalovirus (CMV) with the single-stranded DNA as a template to perform a DNA elongation reaction by a DNA- dependent DNA polymerase. whereupon a double-stranded DNA intermediate having a functional promoter sequence upstream of both terminals is produced, (i) transcribing the single-stranded RNA(-) and RNA(+) increasingly from the double-stranded DNA intermediate by the DNA-dependent RNA polymerase which is capable of recognizing the functional promoter sequence of step (h). and (j) optionally, repeating steps (f) to (i) using the resulting single stranded RNA(-) and RNA(+) as a template in optionally repeated step (f), (k) hybridizing the resulting nucleic acids with
  a capturing probe absorbed to or bound with a solid support which probe contains a nucleic acid sequence comprising at least fifteen continuous bases selected from the nucleic acid sequence of SEQ ID NO:5, SEQ ID NO:6, and/or SEQ ID NO:7, and which optionally may be modified and
  a detecting probe containing a nucleic acid sequence comprising at least fifteen continuous bases selected from the nucleic acid sequence of SEQ ID NO:5, SEQ ID NO:6, and/or SEQ ID NO:7, and which is modified by a label, (l) separating any unreacted detecting probe and (m) measuring the label of the optionally labeled capturing probe, the amplified nucleic acids and the detecting probe.

17. The method of claim 7, wherein the target nucleic acid is extracted from a sample.

18. The method of claim 8, wherein the target nucleic acid is extracted from a sample.

19. The probe of claim 9, wherein the nucleic acid sequence optionally is modified with a label, a linker arm or biotin.

20. The kit of claim 10, wherein the nucleic acid sequnce of the probe optionally is modified with a label, a linker arm or biotin.

21. The method of claim 11, wherein the target nucleic acid is extracted from a sample.

22. The method of claim 12, wherein the target nucleic acid is extracted from a sample.

23. The kit of claim 13, wherein the nucleic acid sequencce of the probe optionally is modified with a label, a linker arm or biotin.

24. The kit of claim 14, wherein the nucleic acid sequence of the probe optionally is modified with a label, a linker arm or biotin.

25. The method of claim 15, wherein the nucleic acid sequence of the probe optionally is modified with a label, a linker arm or biotin.

26. The method of claim 16, wherein the detected label is quantitatively measured.

27. A method for amplifying a nucleic acid of cytomegalovirus (CMV) utilizing a nucleic acid sequence (β2.7), which method comprises:

(a) providing a target nucleic acid consisting of (b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:2, SEQ ID NO:3, OR SEQ ID NO:4, and has a promoter sequence of a DNA-dependent RNA polymerase at the 5'-terminal, with the RNA (+) as a template to elongate the primer by the RNA-dependent DNA polymerase, whereupon an elongated RNA/DNA hybrid is obtained, (c) digesting the RNA in the elongated RNA/DNA hybrid by a ribonuclease H which specially digests only the RNA of the elongated RNA/DNA hybrid, whereupon a single-stranded DNA is obtained, (d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:1, with the single-stranded DNA as a template to perform a DNA elongation reaction by a DNA-dependent DNA polymerase, whereupon a double-stranded DNA intermediate having a functional promoter sequence upstream of the 5'-terminal is produced, (e) transcribing a single-stranded RNA (-) increasingly from the double-stranded DNA intermediate by the DNA-dependent RNA polymerase which is capable of recognizing the functional promoter sequence of step (d), (f) hybridizing the second primer for amplifying a nucleic acid of cytomegalovirus (CMV) with the single stranded RNA (-) obtained in step (e) as a template to perform a DNA elongation reaction by a RNA-dependent DNA polymerase, whereupon an elongated RNA/DNA hybrid is obtained, (g) digesting the RNA in the elongated RNA/DNA hybrid by a ribonuclease H which specially digests only the RNA of the elongated RNA/DNA hybrid, whereupon a single-stranded DNA is obtained, (h) hybridizing the first primer for amplifying a nucleic acid of cytomegalovirus (CMV) with the single-stranded DNA as a template to perform a DNA elongation reaction by a DNA-dependent DNA polymerase, whereupon a double-stranded DNA intermediate having a functional promoter sequence upstream of the 5'-terminal is produced, (i) transcribing the single-stranded RNA (-) increasingly from the double-stranded DNA intermediate by the DNA-dependent RNA polymerase which is capable of recognizing the functional promoter sequence of step (h), and (j) optionally, repeating steps (f) to (i) using the resulting single stranded RNA (-) as a template in optionally repeated step (f).

28. The method of claim 27, wherein the target nucleic acid is extracted from a sample.

29. A method for detecting and/or capturing a nucleic acid of the cytomegalovirus (CMV) utilizing a nucleic acid sequence (β2.7), which comprises:

(a) providing a target nucleic acid consisting of RNA (+);

(b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:2, SEQ ID NO:3, OR SEQ ID NO:4, and has a promoter sequence of a DNA-dependent RNA polymerase at the 5'-terminal, with the RNA (+) as a template to elongate the primer by the RNA-dependent DNA polymerase, whereupon an elongated RNA/DNA hybrid is obtained, (c) digesting the RNA in the elongated RNA/DNA hybrid by a ribonuclease H which specially digests only the RNA of the elongated RNA/DNA hybrid, whereupon a single-stranded DNA is obtained, (d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:1, with the single-stranded DNA as a template to perform a DNA elongation reaction by a DNA-dependent DNA polymerase, whereupon a double-stranded DNA intermediate having a functional promoter sequence upstream of the 5'-terminal is produced, (e) transcribing a single-stranded RNA (-) increasingly from the double-stranded DNA intermediate by the DNA-dependent RNA polymerase which is capable of recognizing the functional promoter sequence of step (d), (f) hybridizing the second primer for amplifying a nucleic acid of cytomegalovirus (CMV) with the single stranded RNA (-) obtained in step (e) as a template to perform a DNA elongation reaction by a RNA-dependent DNA polymerase, whereupon an elongated RNA/DNA hybrid is obtained, (g) digesting the RNA in the elongated RNA/DNA hybrid by a ribonuclease H which specially digests only the RNA of the elongated RNA/DNA hybrid, whereupon a single-stranded DNA is obtained, (h) hybridizing the first primer for amplifying a nucleic acid of cytomegalovirus (CMV) with the single-stranded DNA as a template to perform a DNA elongation reaction by a DNA-dependent DNA polymerase, whereupon a double-stranded DNA intermediate having a functional promoter sequence upstream of both terminals is produced, (i) transcribing the single-stranded RNA(-) and RNA(+) increasingly from the double-stranded DNA intermediate by the DNA-dependent RNA polymerase which is capable of recognizing the functional promoter sequence of step (h), and (j) optionally, repeating steps (f) to (i) using the resulting single stranded RNA(-) and RNA(+) as a template in optionally repeated step (f), and (k) detecting and/or capturing the resulting nucleic acids with a probe for detecting and/or capturing a nucleic acid of the cytomegalovirus (CMV) which probe contains a nucleic acid sequence comprising at least fifteen continuous bases selected from the nucleic acid sequence of SEQ ID NO:5, SEQ ID NO:6, and/or SEQ ID NO:7, or a complementary nucleic acid thereof, wherein the nucleic acid sequence optionally may be modified by a label.

30. The method of claim 31, wherein the nucleic acid sequence of the probe optionally is modified with a label, a linker arm or biotin.

31. A method for detecting a nucleic acid of the cytomegalovirus (CMV) utilizing a nucleic acid sequence (β2.7), which method comprises:

(a) providing a target nucleic acid consisting of RNA (b) hybridizing a first primer for amplifying a nucleic acid of cytomegalovirus (CMV) which first primer contains a nucleic acid sequence comprising at least fifteen continuous bases selected from the nucleic acid sequence of SEQ ID NO:2, SEQ ID NO:3, OR SEQ ID NO:4, and has a promoter sequence of a DNA-dependent RNA polymerase at the 5'-terminal, with the RNA (+) as a template to elongate the primer by the RNA-dependent DNA polymerase, whereupon an elongated RNA/DNA hybrid is obtained, (c) digesting the RNA in the elongated RNA/DNA hybrid by a ribonuclease H which specially digests only the RNA of the elongated RNA/DNA hybrid, whereupon a single-stranded DNA is obtained, (d) hybridizing a second primer for amplifying a nucleic acid of cytomegalovirus (CMV) which second primer contains a nucleic acid sequence comprising at least fifteen continuous bases selected from the nucleic acid sequence of SEQ ID NO:1, with the single-stranded DNA as a template to perform a DNA elongation reaction by a DNA-dependent DNA polymerase, whereupon a double-stranded DNA intermediate having a functional promoter sequence upstream of the 5'-terminal is produced, (e) transcribing a single-stranded RNA (-) increasingly from the double-stranded DNA intermediate by the DNA-dependent RNA polymerase which is capable of recognizing the functional promoter sequence of step (d), (f) hybridizing the second primer for amplifying a nucleic acid of cytomegalovirus (CMV) with the single stranded RNA (-) obtained in the above step (e) as a template to perform a DNA elongation reaction by a RNA-dependent DNA polymerase, whereupon an elongated RNA/DNA hybrid is obtained, (g) digesting the RNA in the elongated RNA/DNA hybrid by a ribonuclease H which specially digests only the RNA of the elongated RNA/DNA hybrid, whereupon a single-stranded DNA is obtained, (h) hybridizing the first primer for amplifying a nucleic acid of cytomegalovirus (CMV) with the single-stranded DNA as a template to perform a DNA elongation reaction by a DNA- dependent DNA polymerase, whereupon a double-stranded DNA intermediate having a functional promoter sequence upstream of both terminals is produced, (i) transcribing the single-stranded RNA(-) and RNA(+) increasingly from the double-stranded DNA intermediate by the DNA-dependent RNA polymerase which is capable of recognizing the functional promoter sequence of step (h), and (j) optionally, repeating steps (f) to (i) using the resulting single stranded RNA(-) and RNA(+) as a template in optionally repeated step (f), (k) hybridizing the resulting nucleic acids with
a capturing probe absorbed to or bound with a solid support which probe contains a nucleic acid sequence comprising at least fifteen continuous bases selected from the nucleic acid sequence of SEQ ID NO:5, SEQ ID NO:6, and/or SEQ ID NO:7, and which optionally may be modified and a detecting probe containing a nucleic acid sequence comprising at least fifteen continuous bases selected from the nucleic acid sequence of SEQ ID NO:5, SEQ ID NO:6, and/or SEQ ID NO:7, and which is modified by a label, (l) separating any unreacted detecting probe and (m) measuring the label of the optionally labeled capturing probe, the amplified nucleic acids and the detecting probe.

32. The method of claim 29, wherein the nucleic acid sequence of the probe optionally is modified with a label, a linker arm or biotin.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PRIMER"

( x i ) SEQUENCE DESCRIPTION: SEQ ID NO:1:

GGGAATCGTC GACTTTGAAT TCTTCGA        2 7

( 2 ) INFORMATION FOR SEQ ID NO:2:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "PRIMER"

( x i ) SEQUENCE DESCRIPTION: SEQ ID NO:2:

GTCCCGACTA CCATCAGCAG TACCA 25

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PRIMER"

( x i ) SEQUENCE DESCRIPTION: SEQ ID NO:3:

GGCCGGTCGG CTTCTGTTTT ATTA 24

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PRIMER"

( x i ) SEQUENCE DESCRIPTION: SEQ ID NO:4:

TCCTTTCCTT AATCTCGGAT TATCA 25

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PROBE"

( x i ) SEQUENCE DESCRIPTION: SEQ ID NO:5:

TTCCCTCTCC TACCTACCAC GAA 23

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PROBE"

( x i ) SEQUENCE DESCRIPTION: SEQ ID NO:6:

CGCAGATGAT AAACAAGAGG GTAA 24

( 2 ) INFORMATION FOR SEQ ID NO:7:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "PROBE"

( x i ) SEQUENCE DESCRIPTION: SEQ ID NO:7:

ACAGACATTT GGGTACCTCA GCTT                                                              2 4

( 2 ) INFORMATION FOR SEQ ID NO:8:

( i ) SEQUENCE CHARACTERISTICS:
              ( A ) LENGTH: 25 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "PROMOTER"

( x i ) SEQUENCE DESCRIPTION: SEQ ID NO:8:

AATTCTAATA CGACTCACTA TAGGG                                                             2 5

( 2 ) INFORMATION FOR SEQ ID NO:9:

( i ) SEQUENCE CHARACTERISTICS:
              ( A ) LENGTH: 17 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "PROMOTER"

( x i ) SEQUENCE DESCRIPTION: SEQ ID NO:9:

ATTAACCCTC ACTAAAG                                                                      1 7

( 2 ) INFORMATION FOR SEQ ID NO:10:

( i ) SEQUENCE CHARACTERISTICS:
              ( A ) LENGTH: 17 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "PROMOTER"

( x i ) SEQUENCE DESCRIPTION: SEQ ID NO:10:

ATTTAGGTGA CACTATA                                                                      1 7

( 2 ) INFORMATION FOR SEQ ID NO:11:

( i ) SEQUENCE CHARACTERISTICS:
              ( A ) LENGTH: 29 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "PROMOTER"

( x i ) SEQUENCE DESCRIPTION: SEQ ID NO:11:

AATTCTAATA CGACTCACTA TAGGGAGGA                                                         2 9